(12) United States Patent
Fantoni et al.

(10) Patent No.: US 9,603,740 B2
(45) Date of Patent: Mar. 28, 2017

(54) DEVICE FOR VITRECTOMY SURGICAL OPERATIONS

(71) Applicant: ERRE QUADRO S.R.L., Pisa (IT)

(72) Inventors: Gualtiero Fantoni, Pisa (IT); Stanislao Rizzo, Lucca (IT); Gionata Ciampi, Pescia (IT)

(73) Assignee: Erre Quadro S.R.L., Pisa (IT)

( * ) Notice: Subject to any disclaimer, the term of this patent is extended or adjusted under 35 U.S.C. 154(b) by 152 days.

(21) Appl. No.: 14/410,800

(22) PCT Filed: Jun. 26, 2013

(86) PCT No.: PCT/IB2013/055267
§ 371 (c)(1),
(2) Date: Dec. 23, 2014

(87) PCT Pub. No.: WO2014/002040
PCT Pub. Date: Jan. 3, 2014

(65) Prior Publication Data
US 2015/0182379 A1 Jul. 2, 2015

(30) Foreign Application Priority Data
Jun. 26, 2012 (IT) .............................. PI2012A0074

(51) Int. Cl.
*A61B 17/32* (2006.01)
*A61F 9/007* (2006.01)

(52) U.S. Cl.
CPC .... *A61F 9/00763* (2013.01); *A61B 17/32002* (2013.01); *A61B 2017/320064* (2013.01)

(58) Field of Classification Search
CPC ...... A61F 9/007; A61F 9/00763; A61B 17/32; A61B 17/32002; A61B 2017/00544; A61B 2017/320064; A61B 17/20
See application file for complete search history.

(56) References Cited

U.S. PATENT DOCUMENTS 5,047,008 A * 9/1991 de Juan, Jr. ......... A61F 9/00763
600/564
5,106,364 A * 4/1992 Hayafuji .......... A61B 17/32002
30/208

FOREIGN PATENT DOCUMENTS

WO    WO 2010/118172 A1    10/2010

\* cited by examiner

*Primary Examiner* — Victor Nguyen
(74) *Attorney, Agent, or Firm* — Woodard, Emhardt, Moriarty, McNett & Henry LLP

(57) ABSTRACT

A vitrectomy probe for removing vitreous material from an eyeball, having a longitudinal axis and an outer tube with a closed end and a lateral surface, at least one inlet port located proximate to the closed end and configured to allow the vitreous material to enter into the outer tube; an inner tube arranged in the outer tube to relatively move with respect to the outer tube, the inner tube having an opening with a cutting profile through which the vitreous material can be cut and can enter the inner tube. A drive unit configured for causing the outer tube and the inner tube to move relatively with respect to each other, in such a way that the cutting profile cuts the vitreous material entering the inlet port.

16 Claims, 5 Drawing Sheets

DEVICE FOR VITRECTOMY SURGICAL OPERATIONS

CROSS-REFERENCE TO RELATED APPLICATION

This application is a National Stage of International Application No. PCT/IB2013/055267 filed Jun. 26, 2013 which claims the foreign priority benefit of Italian Patent Application No. PI2012A000074 filed Jun. 26, 2012, which are hereby incorporated by reference.

FIELD OF THE INVENTION

The present invention relates to a device for vitrectomy surgical operations, and specifically to a vitrectomy probe.

In particular, the invention relates to a specific medical device which can be used for ophthalmic surgical operations, i.e. for treating some eye's diseases and, more in particular, to perform vitrectomy surgical operations.

BACKGROUND OF THE INVENTION

As well known, a vitrectomy surgical operation is an ophthalmic operation performed when the vitreous has become opaque due to hemorrhages, e.g., after a proliferative diabetic retinopathy, inflammation or due to a traction force applied to the retina or the presence of membranes or foreign objects within the eyeball. The vitrectomy surgical operation consists of both removing small fragments of membranes from the retinal surface and the vitreous and replacing it by using an equivalent means, called "vitreous substitute".

The basic device to perform said vitrectomy operation is the vitrectomy probe, which is a pneumatic guillotine configured for performing the aforementioned removal and excision operations. The vitrectomy probe is provided with:
- a handgrip shaped to allow the operator to properly handle the tool;
- an outer tube comprising a slot manufactured on its own lateral surface proximate to one end of the outer tube itself;
- an inner tube that is inserted within the outer tube;
- a command system which creates a depression, i.e. a vacuum degree, within the outer tube and the inner tube, and causes the inner tube to relatively move with respect to the outer tube.

In particular, the command system, thanks to the synergy of the abovementioned depression and relative movement, enables the vitrectomy probe to suck in the vitreous in such a way that the vitreous fragments, attracted by the suction, are cut by the moving edge of the inner tube when the edge overlaps the slot manufactured on the lateral surface of the outer tube.

Examples of a vitrectomy probe can be found in DE 102010 and in U.S. Pat. No. 5,106,364.

However, the above mentioned prior art devices have some relevant drawbacks.

A first significant disadvantage is that the vitrectomy probes are very difficult to be used and great expertise and care are required to the surgeon during the surgical operation, because it is very hard to adjust the suction flow rate in order to perform accurate excision.

In particular, the size and the number of the fragments of vitreous excised by the vitrectomy probe only depend upon the movements and the position of the probe, while the probe is located inside the eye and, therefore, they only depend upon the surgeon skill.

Thus, another drawback is that the surgical vitrectomy operation takes a very long time, since the vitrectomy probe must be extremely accurately handled, which requires very slow movements.

The operation takes a long time also because, in order to reduce the risk of errors, the vitrectomy probes must be set to a very low removal rate, wherein the flow rate periodically changes from zero to a maximum value in a substantially sinusoidal law, due to the slots overlap variation.

Another disadvantage is that the costs of the vitrectomy operations are rather high, due to long duration.

For example, in WO2010118172 a rotary inner tube acts as the internal port of standard vitrectomy probes, but, due to the length of the helical grooves, the suction force is reduced by such features as friction, turbulences, and so on. Moreover, the system can be applied only to rotary vitrectomy probes and the suction has a sinusoidal behaviour whose maximum is limited by the above-mentioned features.

In WO2012059092 and in U.S. Pat. No. 5,106,364, which appears to be the patents most closely related to the invention, the suction is increased through multiples ports made both on the external tube and on the internal one. These solutions can be applied to both rotary and linear/oscillating vitrectomy probes. However, in the described realizations, the suction has a square-wave behaviour, and the traction force continues to pulse accordingly. Moreover, the axial extension of the ports on the external tube is increased, which causes a loss of precision.

SUMMARY OF THE INVENTION

In fact, the technical object that underlies the present invention is a vitrectomy probe capable of substantially obviating the aforementioned drawbacks.

In the context of this technical object, an important object of the present invention is to provide a vitrectomy probe that is easy and simple to use.

Another important object of the invention is to provide a vitrectomy probe which enables the surgeons to perform vitrectomy surgeries quickly and accurately.

Furthermore, another object of the invention is to provide a vitrectomy probe minimizing the oscillating traction forces applied to the retina during the vitrectomy surgeries.

The technical object and the objects described above are achieved by a vitrectomy probe as claimed in annexed claim 1. Preferred embodiments are described in the dependent claims.

According to the invention, a vitrectomy probe for removing vitreous material from an eyeball comprises:
- an outer tube with a closed end and a lateral surface, at least one inlet port being provided through said lateral surface, said inlet port located proximate to said closed end and configured to allow said vitreous material to enter into said outer tube;
- an inner tube arranged in said outer tube to relatively move with respect to said outer tube, said inner tube having an opening with a cutting profile, through which said vitreous material can be cut and can enter said inner tube, said inner tube configured to be connected to a suction unit in order to remove by suction any vitreous material entered into said inner tube;
- a drive unit configured for causing said outer tube and said inner tube to move relatively with respect to each other, in such a way that said cutting profile cuts said vitreous material entering said inlet port;

wherein said cutting profile comprises a cutting portion that extends along a direction that is inclined according to a predetermined inclination angle ($\alpha$) with respect to said longitudinal axis, such that said inclined cutting portion carries out a progressive removal of said vitreous during said relative movement of said inner tube with respect said outer tube.

This way, an almost continuous flow of vitreous material through the inner tube.

Differently to a straight cutting portion, with which the cut is very sudden, the cutting force remains always active; and so the cutting action is continuous like scissors effect, reducing the fatigue effect on the retina.

Preferably, said inclined cutting portion is an additional cutting portion that is added to a main cutting portion which lays in a plane orthogonal to said longitudinal axis.

Advantageously, said inclined cutting portion is arranged on a side surface of said inner tube.

Advantageously, said inclined cutting portion is the edge of an open end of said inner tube facing said closed end of said main tube portion.

In a preferred embodiment, said main cutting portion, is the edge of an open end of said inner tube, facing said closed end of said main tube portion.

Preferably, said inclination angle ($\alpha$) is set between 60° and 30°, in particular between 50° and 40°.

Preferably, said opening is arranged on a side surface of said inner tube and is an elongated hole having two inclined parallel cutting portions.

Preferably, said opening is arranged on a side surface of said inner tube and is a predetermined minimum distance from an end portion of said inner tube, in particular said minimum distance is shorter than a diameter of said at least one inlet port, more in particular shorter than 70% of the axial extension of said at least one inlet port.

Preferably, said opening has a size smaller than said inlet port, in particular less than 50% of said inlet port, more in particular less than 20% of a passage area of said inlet port.

Preferably, said cutting profile of said opening is a curved profile.

Preferably, said opening is a V shaped opening. Alternatively, it can be a circular opening.

Advantageously, a plurality of circular openings is provided aligned to each other and slanted with respect to said longitudinal axis.

Preferably, said internal tube comprises a plurality of openings provided with respective cutting profiles.

Advantageously, said openings extend along respective directions substantially parallel to one another.

BRIEF DESCRIPTION OF THE DRAWINGS

The features and the advantages of the invention are clarified by the following detailed description of the preferred embodiments of the invention, with reference to the accompanying drawings, in which.

DESCRIPTION OF A PREFERRED EXEMPLARY EMBODIMENT

Figures 1, 2, 3:
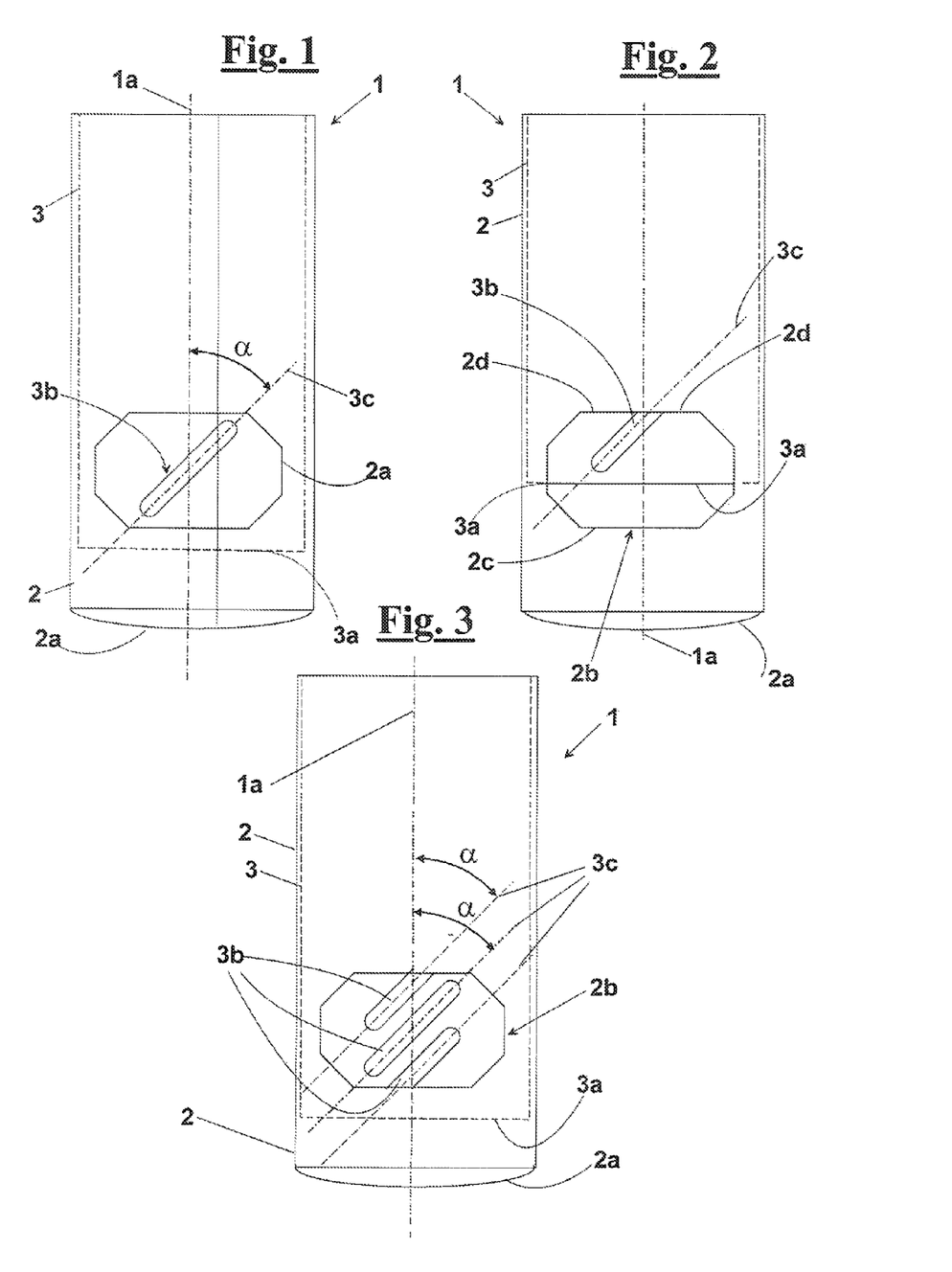
FIGS. 1 and 2 show a front view a portion of a vitrectomy probe, according to an embodiment of the invention, in two different steps of a stroke of inner tube 3 with respect to outer tube 2.
FIG. 3 shows a portion of a vitrectomy probe according to another embodiment of the invention.
Figure 4:
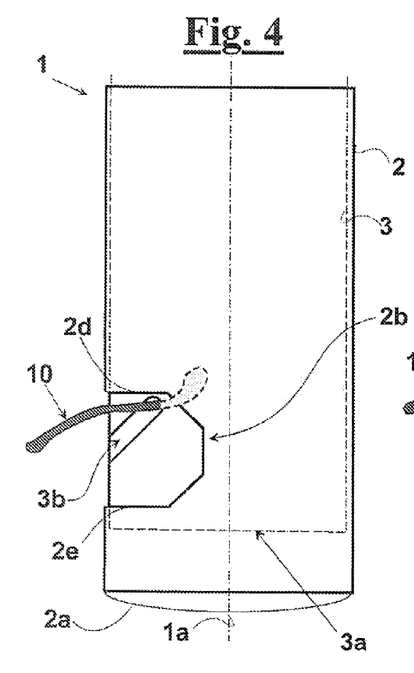
FIGS. 4 and 5 show a side view of the portion of a vitrectomy probe of FIGS. 1 and 2, wherein the cutting action on vitreous is schematically illustrated.

With reference to FIGS. 1 and 2, a vitrectomy probe according to an embodiment of the present invention is globally indicated by reference numeral 1. Vitrectomy probe 1 has a longitudinal axis 1a and comprises, on its active cutting zone, two tubes 2 and 3, preferably two cylindrical tubes, which are mutually movable to cut the material to be removed, consisting of fragments of membranes and vitreous, indistinctly indicated below as "vitreous" 10 (FIGS. 3 and 4). More in detail, vitrectomy probe 1 comprises an outer tube 2 and an inner tube 3 that is at least partially arranged within outer tube 2 and is movable relative thereto along longitudinal axis 1a. The two tubes 2 and 3 can substantially be identified as hollow cylindrical bodies that have respective longitudinal axes substantially coincident with each other and, more specifically, coincident with longitudinal axis 1a. Outer tube 2 has a closed end portion 2a and at least one inlet port 2b which allows vitreous 10 to enter into outer tube 2. Inlet port 2b is manufactured on the lateral surface of outer tube 2, proximate to closed end portion 2a.

In the embodiment shown in FIGS. 1 and 2, inlet port 2b is defined by a proximal contrasting edge 2c next to closed end portion 2a and by a distal contrasting edge 2d farther from closed end portion 2a. In this embodiment, proximal contrasting edge 2c and distal contrasting edge 2d extend along respective directions that, in this case, are substantially parallel to each other and are normal to longitudinal axis 1a. However, contrasting edges 2c and 2d may extend along diverging lines, or even along curved lines. During the cutting step, vitreous 10 collides against edges 2c and 2d, as better described below.

Preferably, inner tube 3 has an open end portion that faces the internal side of closed end portion 2a of outer tube 2. This way, vitreous 10, which flows into vitrectomy probe 1 through inlet port 2b, can also flow into inner tube 3. This end portion has an edge 3a that may be configured as a cutting edge 3a, to provide a cutting section 3a.

Inner tube 3 advantageously has an opening 3b provided with a cutting profile. Opening 3b may be manufactured on a bottom and/or lateral surface thereof. In the latter case, opening 3b is made proximate to bottom surface i.e. bottom end section 3a.

Outer tube 2 and inner tube 3 of probe 1 of FIGS. 1,2 are shown more in detail in FIGS. 14,15 and 16,17, respectively.

In particular, the passage area of opening 3b made on the lateral surface, i.e. a lateral opening 3b of inner tube 3 may be smaller than the passage area of inlet port 2b. Preferably, the passage area of opening 3b is smaller than 50% of the passage area of inlet port 2a and, more preferably, smaller than 20% of the passage area of inlet port 2a.

In particular, the passage area of opening 3b made on the lateral surface of inner tube 3 may be smaller than the passage area of opening made on bottom surface of inner tube 3, if any.

In particular, inner tube 3 may have only one lateral opening 3b (FIGS. 1, 2, 4 and 5) which extends along a extension direction 3c, i.e. an extension direction 3c. In alternative, inner tube 3 may have a plurality of lateral openings 3b (FIGS. 3 and 6-11). In this case, extension directions 3c, of openings 3b may be substantially parallel to one another (FIGS. 3,6-11). In the same case, the lengths of lateral openings 3b, measured substantially along extension directions 3c, are advantageously equal to one another. In the same case, the passage areas of lateral openings 3b are substantially equal to one another.

Advantageously, extension direction 3c of lateral openings 3b is transverse to longitudinal axis 1a and/or to contrasting edges 2c and/or 2d. In particular, as shown in the drawings, extension direction 3c is oblique with respect to longitudinal axis 1a. In other words, extension direction 3c forms an inclination angle α smaller than 90°, with respect to longitudinal axis 1a. More in detail, inclination angle α is smaller than 80°, preferably inclination angle α is set between 60° and 30° and, more preferably, inclination angle α is set between 50° and 40°.

The profile of lateral opening 3b comprises at least one cutting edge configured for carrying out a removal of vitreous 10. This cutting edge is parallel to extension direction 3c and, therefore, is transversal with respect to contrasting edges 2c and 2d such that, during the mutual movement of two tubes 2 and 3, it carries out a guillotine-type cutting action, i.e. a continuous and progressive cutting action similar to the cutting action performed by scissors or by a cutter, as better described below. In detail, lateral opening 3b may comprise two cutting edges that are preferably substantially parallel to extension direction 3c. More in detail, opening 3b may comprise a distal cutting edge 3d farther from cutting section 3a, which in use is located farther from the inner of the patient and a proximal cutting edge 3e closer to cutting section 3a, which in use is located closer to the inner of the patient. When inner tube 3 approaches closed end portion 2a, distal cutting edge 3d removes vitreous 10 through the guillotine-type cut, i.e. by squeezing vitreous 10 between distal cutting edge 3d and proximal contrasting edge 2c. When inner tube 3 moves away from closed end portion 2a, cutting edge 3e removes vitreous 10 through a similar guillotine-type cut, i.e. by squeezing vitreous 10 between proximal cutting edge 3e and distal contrasting edge 2d.

With reference to FIGS. 6-11, in other embodiments, each lateral opening 3b consists of a plurality of holes, for instance cylindrical holes (FIGS. 9 and 11), whose centre points belong to extension directions 3c, still oblique with respect to longitudinal axis 1a according to aforementioned inclination angle α.

Figure 7:
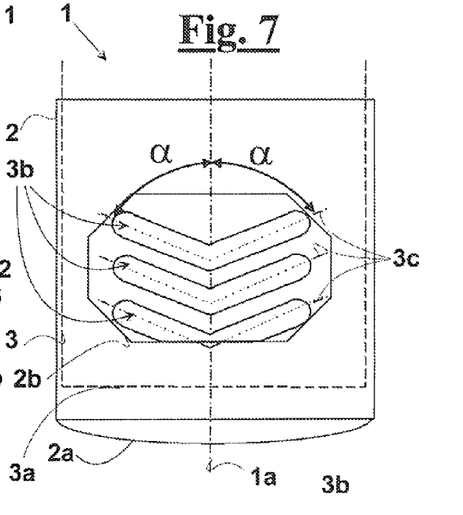
Figure 8:
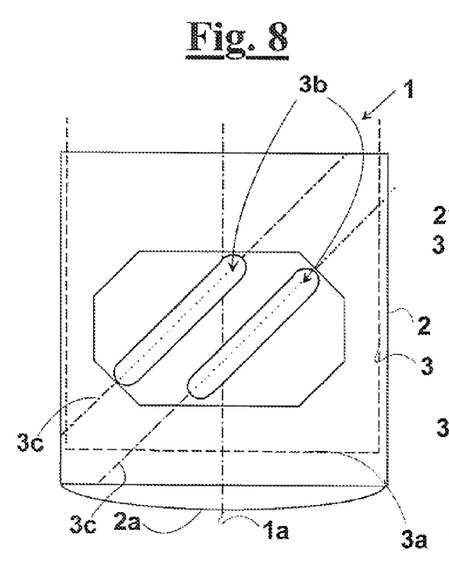
Figure 9:
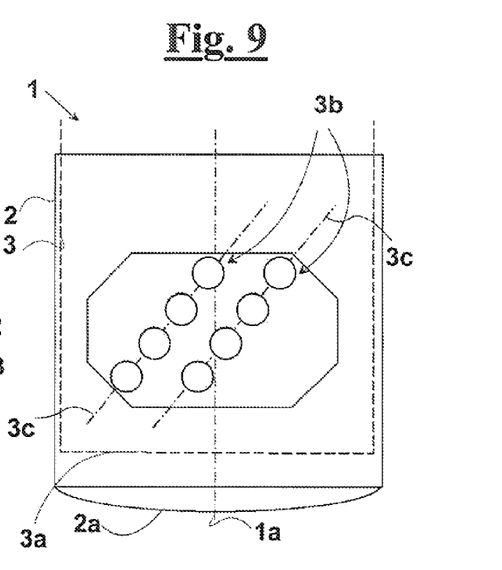

In some embodiments, as shown in FIGS. 7 and 8, each lateral opening 3b consists of two adjacent slots of substantially the same length. The axes of these slots form inclination angles α with longitudinal axis 1a. In particular (FIG. 8) the slot may have two arms with respective inclination angles α that are opposite to each other and have preferably substantially the same amplitude.

Inclination angle or angles α preferably have an amplitude narrower than 90°, more preferably have an amplitude set between 60° and 30° and even more preferably, an amplitude set between 50° and 40°.

Figure 10:
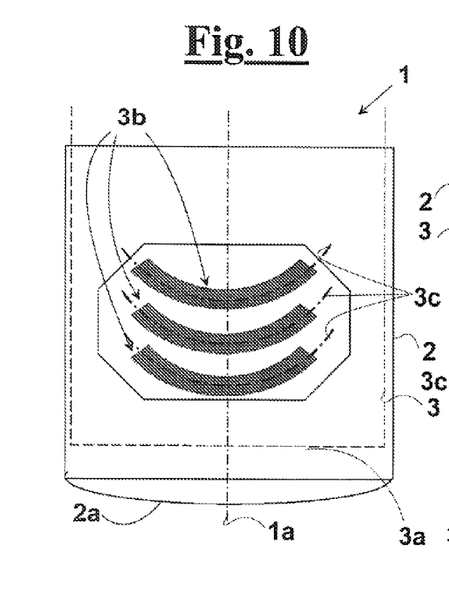
Figure 11:
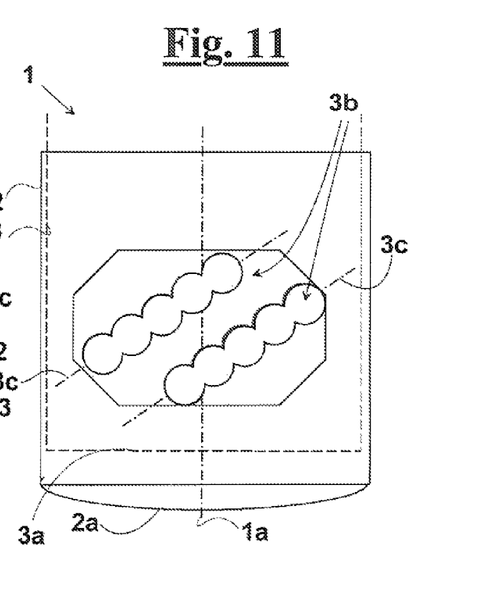

In another embodiment, as shown in FIG. 10, a lateral section, or lateral sections 3b consist/s of curved profiles having curved extension directions 3c, whose centre points are substantially aligned along the direction of longitudinal axis 1a. Curved extension directions 3c are preferably symmetrical with respect to longitudinal axis 1a, therefore, they are transverse with respect to longitudinal axis 1a.

It should be noted that, in each of the above-mentioned embodiments, the minimum distance from at least one of proximal cutting edges 3e of lateral openings 3b from cutting section 3a, measured along longitudinal axis 1a, is advantageously shorter than the axial length inlet port 2b, i.e. than the distance between two contrasting cutting edges 2c and 2d, measured along the direction of longitudinal axis 1a.

Accordingly, in the case of openings made through both lateral and bottom surfaces of inner tube 3, at least one of bottom and lateral openings 3a, 3b falls within inlet port 2b in any current relative position of tubes 2 and 3. More in particular, the aforementioned minimum distance is shorter than 90% of the axial length of inlet port 2b and, more conveniently, is shorter than 75% of this axial length.

In a further embodiment, not shown, vitrectomy probe 1 is provided with a handgrip on the opposite side of closed end portion 2a, in order to enable the operator to comfortably handle the device, possibly along with a drive unit associated with vitrectomy probe 1.

In detail, the drive unit is configured for causing inner tube 3 to relatively move with respect to outer tube 2, preferably along longitudinal axis 1a and, at the same time, to create a depression, i.e. a vacuum degree, at least within inner tube 3, such that a suction force is created and applied to vitreous 10 which is removed by cutting sections 3a and 3b. Furthermore, the drive unit allows to adjust the stroke of inner tube 3 in order to regulate the action of opening 3b. A suitable drive unit is described, for instance, in EP2168540A1, paragraphs [0005]-[0051].

Figure 12:
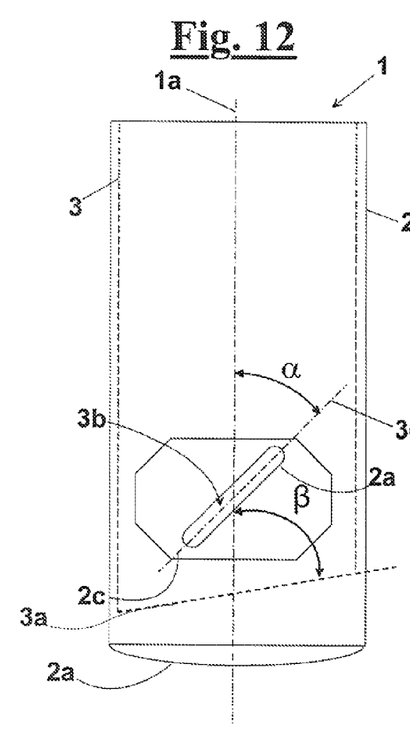
FIGS. 12 and 13 show a front view a portion of a vitrectomy probe, according to a still further embodiment of the invention, in two different steps of a stroke of inner tube 3 with respect to outer tube 2.
Figure 13:
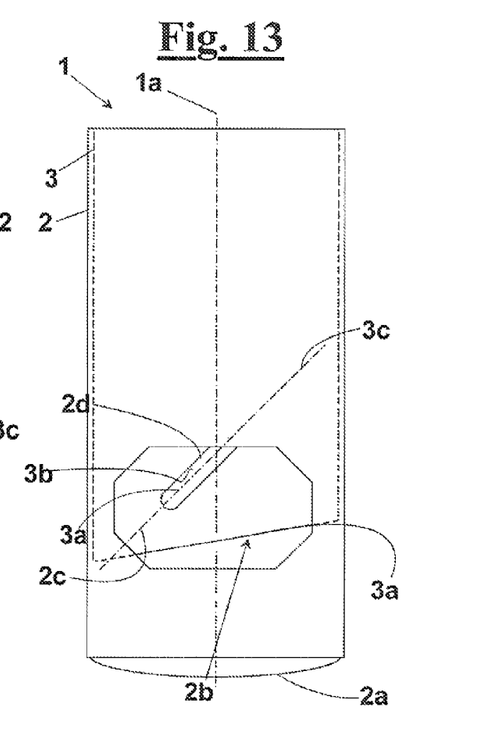
Figure 14:
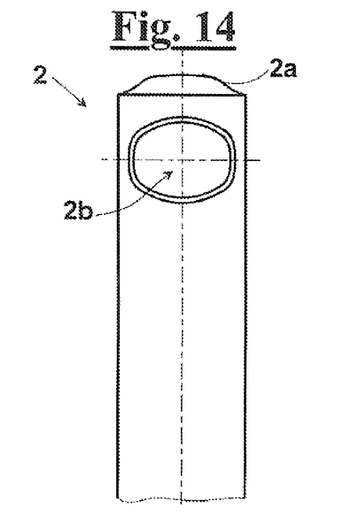
FIGS. 14 and 15 show a front and a lateral view, respectively, of an outer tube of a vitrectomy probe.
Figure 15:
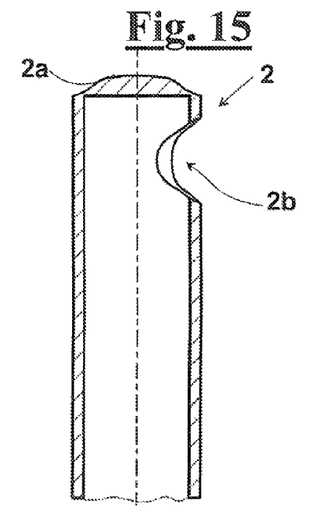
Figure 16:
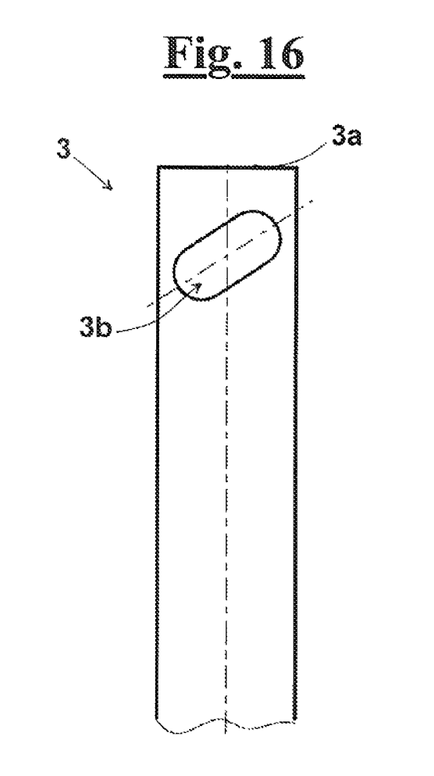
FIGS. 16 and 17 show a front and a lateral view, respectively, of an inner tube of a vitrectomy probe like in FIGS. 1,2.
Figure 17:
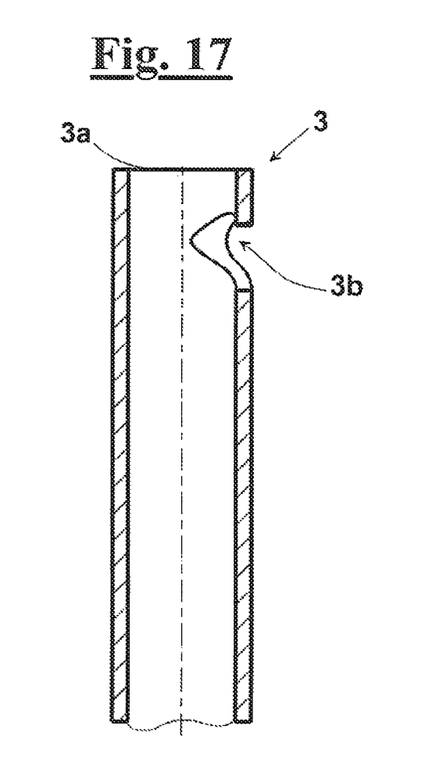

In an embodiment, as shown in FIGS. 12 and 13, a bottom opening is provided through a bottom surface 3a of inner tube 3. Advantageously, bottom surface 3a is slanted with respect to longitudinal axis 1a. More in detail, inclination angle β is smaller than 80°, preferably inclination angle α is set between 60° and 30° and, more preferably, inclination angle β is set between 50° and 40°. FIGS. 12 and 13 show steps of a stroke of inner tube 3 with respect to outer tube 2 as in FIGS. 1 and 2.

The operation of vitrectomy probe 1, whose exemplary embodiments were described above, will now be described. Once the active portion of the probe, i.e. at least a portion of duct 2 and 3, has been inserted into the eyeball, the drive unit is switched on and operated to cause inner tube 3 to translate, in an alternative motion, with respect to outer tube 2, substantially along longitudinal axis 1a. Almost simultaneously, the drive unit creates a depression within inner tube 3.

At the beginning, inner tube 3 is basically completely inserted within outer tube 2, in other words opening 3b falls within inlet port 2a, as shown in FIGS. 1 and 12. Inner tube 3 begins to translate and, at the same time, due to the depression created within inner tube 3, vitreous 10 is sucked both through port 2a and through section 3b. Vitreous 10 is squeezed between proximal cutting edge 3e and distal contrasting edge 2d and, accordingly, fibrous material thereof is cut due to guillotine-type cutting motion of inner tube 3 with respect to outer tube 2. Afterwards, cut vitreous 10 enters into inner tube 3 and is sucked away.

Figure 5:
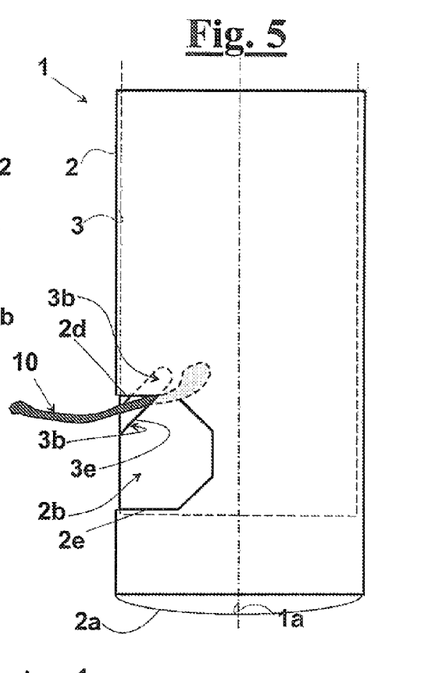
Figure 6:
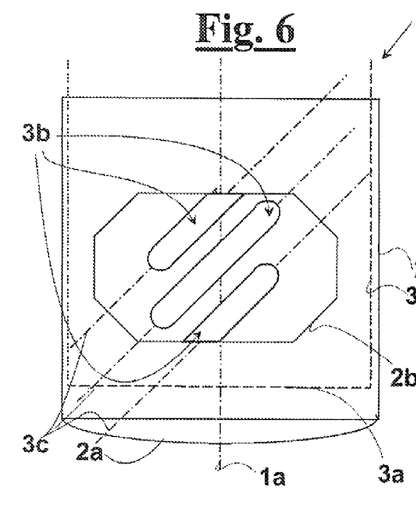
FIGS. 6 to 11 show vitrectomy probes according to further embodiments of the invention.

Subsequently, due to the alternative motion of tubes 2 and 3, cutting section 3a overlaps inlet port 2b, such that vitreous 10 enters into cutting section 3a. Inner tube 3 reverses its travel direction so that vitreous 10 is squeezed between closed end portion 2a and cutting section 3a and is cut by the cutting edge of section 3a. Afterwards, vitreous 10 passes into inner tube 3 and is after sucked away. Finally, due to the above motion reversal, lateral or bottom opening 3b of inner tube 3 overlaps again inlet port 2b, leading to a guillotine-type cut of vitreous 10 by distal cutting edge 3d and proximal contrasting edge 2c, as shown in FIG. 5.

The present invention has significant advantages.

A first advantage is that vitrectomy probe 1, by continuously removing a constant amount of vitreous 10, applies traction forces to the eye that are lower and more constant throughout the whole stroke of inner tube 3, with respect to the above mentioned prior art vitrectomy probe and, accordingly, it causes stress and fatigue effects to the eye that are extremely lower than in the case of any above mentioned prior art vitrectomy probe.

Another significant advantage is achieved due the very high cut precision and quality that is performed by vitrectomy probe 1 and, in particular, thanks to the capability of both lateral and bottom lateral openings 3b to act like a double, or multiple, guillotine.

In particular, lateral openings 3b, not realized next to the end of inner tube 3, which is next to cutting section 3a, comprises two cutting edges 3d and 3e that allow to perform, during each cycle of vitrectomy probe 1, two excisions of vitreous 10 besides the cut that is ordinarily obtained through a possible cutting section 3a.

Another advantage is that vitrectomy probe 1 can perform, at each cycle of inner tube 3, a cut that is progressive and substantially continuous thanks to the specific inclination angle α and/or β between cutting edges 3d and 3e and or bottom opening 3a and contrasting edges 2c and 2d.

In fact, as shown in FIG. 2, the presence of at least one lateral opening 3b and, more specifically, the specific ratio between the distance from one of proximal cutting edges 3e and the cutting section 3a, on one hand, and the distance from contrasting cutting edges 2c and 2d, on the other hand, advantageously causes an overlap between inlet port 2a and at least one of two cutting sections 3a and 3b. Therefore, the above specific ratio between the aforementioned distances allows an almost uninterrupted cutting action.

This feature also ensures that vitreous 10 is always subjected to a restoring force. Moreover, this restoring force changes gradually, unlike in the case of conventional vitrectomy probes, in which the restoration force pulses and changes almost instantaneously from its maximum value to zero.

The foregoing description of an embodiment of the device according to the invention, and of the way of using the apparatus, will so fully reveal the invention according to the conceptual point of view, such that others, by applying current knowledge, will be able to modify and/or adapt for several applications such embodiment without further research and without parting from the invention, and, accordingly, it is therefore to be understood that such adaptations and modifications will have to be considered as equivalent to the specific embodiments. The means and the materials to realise the different functions described herein could have a different nature without, for this reason, departing from the field of the invention. It is to be understood that the phraseology or terminology that is employed herein is for the purpose of description and not of limitation.

The invention claimed is:

1. A vitrectomy probe for removing vitreous material from an eyeball, said vitrectomy probe having a longitudinal axis and comprising:
    an outer tube with a closed end and a lateral surface, at least one inlet port being provided through said lateral surface, said inlet port located proximate to said closed end and configured to allow said vitreous material to enter into said outer tube;
    an inner tube arranged in said outer tube to relatively move with respect to said outer tube, said inner tube having an open end with a main cutting portion and a lateral opening with an additional cutting portion, through which said vitreous material can be cut and can enter said inner tube, said inner tube configured to be connected to a suction unit in order to remove by suction any vitreous material entered into said inner tube;
    a drive unit configured for causing said outer tube and said inner tube to move relatively with respect to each other, in such a way that said cutting profile cuts said vitreous material entering said inlet port;
    wherein the additional cutting portion extends along a direction that is inclined according to a predetermined inclination angle with respect to said longitudinal axis, such that said inclined cutting portion carries out a progressive removal of said vitreous during said relative movement of said inner tube with respect said outer tube;
    wherein said inclined cutting portion is arranged on a side surface of said inner tube; and
    wherein said main cutting portion is the edge of an open end of said inner tube, facing said closed end of said main tube portion.

2. The vitrectomy probe according to claim 1, wherein the main cutting portion lays in a plane orthogonal to said longitudinal axis.

3. The vitrectomy probe according to claim 1, wherein said inclined cutting portion is arranged on a side surface of said inner tube.

4. The vitrectomy probe according to claim 1, wherein said main cutting portion, is an inclined edge of an open end of said inner tube, facing said closed end of said main tube portion.

5. The vitrectomy probe according to claim 1, wherein said inclination angle is set between 60° and 30°, in particular between 50° and 40°.

6. The vitrectomy probe according to claim 1, wherein said opening is arranged on a side surface of said inner tube and is an elongated hole having two inclined parallel cutting portions.

7. The vitrectomy probe according to claim 1, wherein said opening is arranged on a side surface of said inner tube and is a predetermined minimum distance from an end portion of said inner tube, in particular said minimum distance is shorter than a diameter of said at least one inlet port, more in particular shorter than 70% of the axial extension of said at least one inlet port.

8. The vitrectomy probe according to claim 1, wherein said opening has a size smaller than said inlet port, in particular less than 50% of said inlet port, more in particular less than 20% of a passage area of said inlet port.

9. The vitrectomy probe according to claim 1, wherein said cutting profile of said opening is a curved profile.

10. The vitrectomy probe according to claim 1, wherein said opening is a V shaped opening.

11. The vitrectomy probe according to claim 1, wherein said opening is a circular opening.

12. The vitrectomy probe according to claim 11, wherein a plurality of circular openings is provided aligned to each other and slanted with respect to said longitudinal axis.

13. The vitrectomy probe according to claim 1, wherein said internal tube comprises a plurality of openings provided with respective cutting profiles.

14. The vitrectomy probe according to claim 12, wherein said openings extend along respective directions substantially parallel to one another.

15. A vitrectomy probe for removing vitreous material from an eyeball, said vitrectomy probe having a longitudinal axis and comprising:
- an outer tube with a closed end and a lateral surface, at least one inlet port being provided through said lateral surface, said inlet port located proximate to said closed end and configured to allow said vitreous material to enter into said outer tube;
- an inner tube arranged in said outer tube to relatively move with respect to said outer tube, said inner tube having an opening with a cutting profile, through which said vitreous material can be cut and can enter said inner tube, said inner tube configured to be connected to a suction unit in order to remove by suction any vitreous material entered into said inner tube;
- a drive unit configured for causing said outer tube and said inner tube to move relatively with respect to each other, in such a way that said cutting profile cuts said vitreous material entering said inlet port;
- wherein said cutting profile comprises a cutting portion that extends along a direction that is inclined according to a predetermined inclination angle with respect to said longitudinal axis, such that said inclined cutting portion carries out a progressive removal of said vitreous during said relative movement of said inner tube with respect said outer tube;
- wherein said inclined cutting portion is in addition to a first cutting portion orthogonal to said longitudinal axis;
- wherein said inclined cutting portion is arranged on a side surface of said inner tube; and
- wherein said first cutting portion, is the edge of an open end of said inner tube, facing said closed end of said outer tube.

16. A vitrectomy probe for removing vitreous material from an eyeball, said vitrectomy probe having a longitudinal axis and comprising:
- an outer tube with a closed end and a lateral surface, at least one inlet port being provided through said lateral surface, said inlet port located proximate to said closed end and configured to allow said vitreous material to enter into said outer tube;
- an inner tube arranged in said outer tube to relatively move with respect to said outer tube, said inner tube having an open end with a main cutting portion and a lateral opening with an additional cutting portion, through which said vitreous material can be cut and can enter said inner tube, said inner tube configured to be connected to a suction unit in order to remove by suction any vitreous material entered into said inner tube;
- a drive unit configured for causing said outer tube and said inner tube to move relatively with respect to each other, in such a way that said cutting profile cuts said vitreous material entering said inlet port;
- wherein the additional cutting portion extends along a direction that is inclined according to a predetermined inclination angle with respect to said longitudinal axis, such that said inclined cutting portion carries out a progressive removal of said vitreous during said relative movement of said inner tube with respect said outer tube;
- wherein the main cutting portion is an inclined edge of an open end of said inner tube, facing said closed end of said main tube portion.

* * * * *

UNITED STATES PATENT AND TRADEMARK OFFICE
CERTIFICATE OF CORRECTION

PATENT NO. : 9,603,740 B2  
APPLICATION NO. : 14/410800  
DATED : March 28, 2017  
INVENTOR(S) : Gualtiero Fantoni

Page 1 of 1

It is certified that error appears in the above-identified patent and that said Letters Patent is hereby corrected as shown below:

On the Title Page

In item (30) Foreign Application Priority Data, please correct the foreign priority application number to --PI2012A000074--.

Signed and Sealed this  
Sixth Day of June, 2017

Michelle K. Lee  
*Director of the United States Patent and Trademark Office*